United States Patent
Thayer et al.

(12)

(10) Patent No.: US 8,467,049 B2
(45) Date of Patent: Jun. 18, 2013

(54) MANHOLE MODELER USING A PLURALITY OF SCANNERS TO MONITOR THE CONDUIT WALLS AND EXTERIOR

(75) Inventors: Scott M. Thayer, Pittsburgh, PA (US); Eric C. Close, Scwickley, PA (US); Adam Slifko, Pittsburgh, PA (US); Subramanian Vallapuzha, Pittsburgh, PA (US)

(73) Assignee: RedzoneRobotics, Inc., Pittsburgh, PA (US)

( * ) Notice: Subject to any disclaimer, the term of this patent is extended or adjusted under 35 U.S.C. 154(b) by 0 days.

(21) Appl. No.: 11/856,698

(22) Filed: Sep. 17, 2007

(65) Prior Publication Data

US 2008/0068601 A1 Mar. 20, 2008

Related U.S. Application Data

(60) Provisional application No. 60/844,978, filed on Sep. 15, 2006.

(51) Int. Cl.
*G01N 21/00* (2006.01)

(52) U.S. Cl.
USPC ............................... 356/241.5; 356/241.1

(58) Field of Classification Search
USPC ..................... 356/241.1–241.6, 614, 625; 250/559.21–559.22; 73/865.8
See application file for complete search history.

(56) References Cited

U.S. PATENT DOCUMENTS

| | | | |
|---|---|---|---|
| 3,562,642 A | 2/1971 | Hochschild | |
| 3,672,785 A | 6/1972 | Byrne | |
| 3,732,701 A | 5/1973 | Lynch | |
| 4,025,360 A | 5/1977 | Horne | |
| 4,029,428 A | 6/1977 | Levens | |
| 4,179,216 A * | 12/1979 | Theurer et al. | 356/4.01 |
| 4,197,908 A | 4/1980 | Davis et al. | |
| 4,281,447 A | 8/1981 | Miller et al. | |
| 4,285,239 A | 8/1981 | Heine et al. | |
| 4,406,030 A | 9/1983 | Platts | |
| 4,431,017 A | 2/1984 | Willemsen | |
| 4,437,526 A | 3/1984 | Gloor | |
| 4,442,891 A | 4/1984 | Wood | |

(Continued)

FOREIGN PATENT DOCUMENTS

| | | |
|---|---|---|
| AT | 397432 | 8/1993 |
| EP | 462527 | 12/1991 |

(Continued)

OTHER PUBLICATIONS

Remote Orbital Installations LLC, website, roi360.com/equipment.html; date unknown.

(Continued)

*Primary Examiner* — Tarifur Chowdhury
*Assistant Examiner* — Michael P Lapage
(74) *Attorney, Agent, or Firm* — Ference & Associates LLC

(57) ABSTRACT

Methods and apparatuses for inspecting manholes or other voids and collecting data in a comprehensive, repeatable, and measurable manner. A sensor head is suspended and lowered into a manhole or other void. The sensor head collects data related to the condition of the manhole or void walls, and locations of defects, damage, or lateral pipe openings. The data can then be processed to provide a three-dimensional model of the manhole or void, and can be compared to previous or future data.

24 Claims, 3 Drawing Sheets

U.S. PATENT DOCUMENTS

| | | | |
|---|---|---|---|
| 4,521,685 | A | 6/1985 | Rebman |
| 4,577,388 | A | 3/1986 | Wood |
| 4,613,812 | A | 9/1986 | Gelston, II |
| 4,630,676 | A | 12/1986 | Long, Jr. |
| 4,648,454 | A | 3/1987 | Yarnell |
| 4,701,988 | A | 10/1987 | Wood |
| 4,724,108 | A | 2/1988 | Jurgenlohmann et al. |
| 4,725,883 | A * | 2/1988 | Clark et al. .................. 348/84 |
| 4,765,173 | A | 8/1988 | Schellstede |
| 4,819,721 | A | 4/1989 | Long, Jr. |
| 4,822,211 | A | 4/1989 | Shinoda et al. |
| 4,839,936 | A | 6/1989 | Prange |
| 4,862,808 | A | 9/1989 | Hedgcoxe et al. |
| 4,951,758 | A | 8/1990 | Sonku et al. |
| 4,955,951 | A | 9/1990 | Nemoto et al. |
| 5,018,545 | A | 5/1991 | Wells |
| 5,044,824 | A | 9/1991 | Long, Jr. et al. |
| 5,063,780 | A | 11/1991 | Landry et al. |
| 5,088,553 | A | 2/1992 | Ralston et al. |
| 5,094,570 | A | 3/1992 | LaCombe et al. |
| 5,105,882 | A | 4/1992 | Ralston et al. |
| 5,150,989 | A | 9/1992 | Long, Jr. et al. |
| 5,195,392 | A | 3/1993 | Moore et al. |
| 5,197,540 | A | 3/1993 | Yagi et al. |
| 5,203,646 | A | 4/1993 | Landsberger et al. |
| 5,272,986 | A | 12/1993 | Smart |
| 5,318,395 | A | 6/1994 | Driver |
| 5,329,824 | A | 7/1994 | Carapezza |
| 5,387,092 | A | 2/1995 | Pettitt |
| 5,454,276 | A | 10/1995 | Wernicke |
| 5,520,569 | A | 5/1996 | Endoh |
| 5,565,633 | A | 10/1996 | Wernicke |
| 5,571,977 | A | 11/1996 | Kipp |
| 5,574,223 | A | 11/1996 | Kiefer |
| 5,577,864 | A | 11/1996 | Wood et al. |
| 5,608,847 | A | 3/1997 | Pryor |
| 5,700,110 | A | 12/1997 | Kamiyama et al. |
| 5,736,821 | A | 4/1998 | Suyama |
| 5,742,517 | A | 4/1998 | Van Den Bosch |
| 5,773,984 | A | 6/1998 | Suyama et al. |
| 5,878,783 | A | 3/1999 | Smart |
| 5,892,163 | A * | 4/1999 | Johnson ..................... 73/865.8 |
| 5,940,920 | A | 8/1999 | Hare et al. |
| 5,947,051 | A | 9/1999 | Geiger |
| 5,947,213 | A | 9/1999 | Angle et al. |
| 5,960,882 | A | 10/1999 | Polivka |
| 5,975,878 | A | 11/1999 | Wood et al. |
| 5,992,247 | A | 11/1999 | Manestar |
| 6,026,911 | A | 2/2000 | Angle |
| 6,031,371 | A | 2/2000 | Smart |
| 6,039,079 | A | 3/2000 | Kicst, Jr. |
| 6,056,017 | A | 5/2000 | Kamiyama et al. |
| 6,062,948 | A * | 5/2000 | Schiff et al. ..................... 451/9 |
| 6,068,725 | A | 5/2000 | Tweedie et al. |
| 6,082,411 | A | 7/2000 | Ward |
| 6,135,698 | A | 10/2000 | Bonora et al. |
| 6,141,810 | A | 11/2000 | Allen et al. |
| 6,155,363 | A | 12/2000 | Matsumoto et al. |
| 6,162,171 | A | 12/2000 | Ng et al. |
| 6,175,380 | B1 | 1/2001 | Van Den Bosch |
| 6,243,657 | B1 | 6/2001 | Tuck et al. |
| 6,377,734 | B1 | 4/2002 | Mayr et al. |
| 6,378,627 | B1 | 4/2002 | Tubel et al. |
| 6,386,797 | B1 | 5/2002 | Gearhart |
| 6,427,602 | B1 | 8/2002 | Hovis et al. |
| 6,431,270 | B1 | 8/2002 | Angle |
| 6,450,104 | B1 | 9/2002 | Grant et al. |
| 6,491,612 | B1 | 12/2002 | Kurup et al. |
| 6,621,516 | B1 * | 9/2003 | Wasson et al. .................. 348/84 |
| 6,684,706 | B2 | 2/2004 | Knight et al. |
| 6,695,013 | B2 | 2/2004 | Warren |
| 6,697,710 | B2 | 2/2004 | Wilcox |
| 6,745,955 | B2 | 6/2004 | Kronz |
| 6,843,317 | B2 | 1/2005 | Mackenzie |
| 6,853,200 | B2 | 2/2005 | Munser et al. |
| 6,887,014 | B2 | 5/2005 | Holland |
| 6,956,348 | B2 | 10/2005 | Landry et al. |
| 6,964,309 | B2 | 11/2005 | Quinn et al. |
| 7,009,698 | B2 * | 3/2006 | Drost et al. .................. 356/241.1 |
| 7,042,184 | B2 | 5/2006 | Oleynikov et al. |
| 7,073,979 | B2 | 7/2006 | McGrew et al. |
| 7,126,303 | B2 | 10/2006 | Farritor et al. |
| 7,131,791 | B2 | 11/2006 | Whittaker et al. |
| 7,137,465 | B1 | 11/2006 | Kerrebrock et al. |
| 7,148,962 | B2 * | 12/2006 | Fuhrland et al. ............ 356/241.1 |
| 7,191,191 | B2 | 3/2007 | Peurach et al. |
| 7,210,364 | B2 | 5/2007 | Ghorbel et al. |
| 7,386,365 | B2 | 6/2008 | Nixon |
| 7,434,757 | B2 | 10/2008 | Beckham |
| 7,557,914 | B2 * | 7/2009 | Thompson et al. ......... 356/241.1 |
| 7,720,570 | B2 | 5/2010 | Close et al. |
| 2002/0062177 | A1 | 5/2002 | Hannaford et al. |
| 2003/0089267 | A1 | 5/2003 | Ghorbel et al. |
| 2003/0164952 | A1 * | 9/2003 | Deichmann et al. ........... 356/603 |
| 2003/0172871 | A1 | 9/2003 | Scherer |
| 2003/0198374 | A1 | 10/2003 | Hagene et al. |
| 2003/0212472 | A1 | 11/2003 | McKee |
| 2003/0216836 | A1 | 11/2003 | Treat et al. |
| 2004/0006864 | A1 | 1/2004 | Batrin |
| 2004/0021858 | A1 * | 2/2004 | Shima et al. ................ 356/241.1 |
| 2004/0055746 | A1 | 3/2004 | Ross et al. |
| 2004/0088080 | A1 | 5/2004 | Song et al. |
| 2004/0175235 | A1 | 9/2004 | Whittaker et al. |
| 2004/0211894 | A1 * | 10/2004 | Hother et al. ................ 250/269.1 |
| 2005/0104600 | A1 | 5/2005 | Cotton |
| 2005/0288819 | A1 | 12/2005 | de Guzman |
| 2006/0060216 | A1 | 3/2006 | Woo |
| 2006/0066847 | A1 * | 3/2006 | Penza ........................ 356/241.1 |
| 2006/0074525 | A1 | 4/2006 | Close et al. |
| 2006/0287835 | A1 | 12/2006 | Sheth et al. |
| 2006/0290779 | A1 | 12/2006 | Reverte et al. |
| 2007/0019181 | A1 * | 1/2007 | Sinclair et al. ................ 356/4.01 |
| 2007/0153918 | A1 | 7/2007 | Rodriguez |

FOREIGN PATENT DOCUMENTS

| | | |
|---|---|---|
| GB | 2091611 | 8/1982 |
| JP | 10286878 | 10/1998 |
| WO | WO2004095071 A2 * | 11/2004 |

OTHER PUBLICATIONS

Remote Orbital Installations LLC, TRANSPOD Product Brochure; date unknown.

Cues Inc., CUES-IMX Product Brochure; date unknown.

Cues Inc., Quick ZoomCam Product Brochure; date unknown.

EPA Collection Systems O&M Fact Sheet Sewer Cleaning and Inspection, United States Environmental Protection Agency, Office of Water, EPA 832-F-99-031, Sep. 1999.

Hirose, et al., Design of In-Pipe Inspection Vehicles phi50, phi150 pipes, IEEE, pp. 2309-2314, 1999.

Kawaguchi, et al., An Efficient Algorithm of Path Planning for an Internal Gas Pipe Inspection Robot, IEEE, pp. 1155-1160, 1992.

Bertetto, et al., Robot Flessibile a Basso Costo Per Ispezioni Tubi, Internet, pp. 1477, 2001.

Torboin, Advanced Inspection Robot for Unpiggable Pipelines, Internet, pp. 1-9, 2006.

Jin-Wu et al., A Pipeline Inspection Micro Robot Based on Screw Motion Wheels, Internent, 2000, p. 235-238.

Kawaguchi et al., Internal Pipe Inspection Robot, 1995, IEEE, p. 857-862.

Ryew et al., Inpipe Inspection Robot System with Active Steering Mechanism, 2000, IEEE, p. 1652-1657.

Ono et al, Development of an In-pipe Inspection Robot Movable for a Long Distance, 2001, Internet, p. 1-4.

Choi et al., Development of Articulated Robot for Inspection of Underground Pipelines, 1999, Internet, p. 407-414.

Grobmann et al., A Robot Control System Integrating Reactive Control, Reasoning, and Execution Monitoring, 2002, Internet p. 1-16.

Musliner et al, Execution Monitoring and Recovery Planning with Time, 1991, p. 1-4.

Jeng et al., Reliable Automated Manufacturing System Design Based on SMT Framework, 1998, Internet, p. 121-147.

Schempf et al., Neptune: Above-Ground Storage Tank Inspection Robot System, 1995, IEEE, p. 1-7.

Choi et al., Feeder Pipe Inspection Robot With an Inch-Worm Mechanism Using Pneumatic Actuators, International Journal of Control, Automation, and Systems, vol. 4, No. 1, Feb., 2006, p. 87-95.

Silva, Intelligent Control of Robotic Systems with Application in Industrial Process, 1997, p. 221-237.

Nitzan, Three-Dimensional Vision Structure for Robot Applications, IEEE, 1988, p. 291-309.

Yamada et al., A Method of 3D Object Reconstruction by Fusing Vision with Touch Sensing Using Internal Models with Global and Local Deformations, IEEE, 1993, p. 782-787.

Gu et al., Interpretation of Mechanical Impedance Profiles for Intelligent Control of Robotic Meat Processing, IEEE, 1996, p. 507-512.

Jung et al., Adaptive Force Tracking Impedance Control of Robot for Cutting Nonhomogeneous Workpiece, IEEE, 1999, p. 1800-1805.

Wang et al., Application of Force Control on the Working Path Tracking, Journal of Marine Science and Technology, vol. 10, No. 2, 2002, p. 98-103.

Xiao et al., Sensor-Based Hybrid Position/Force Control of a Robot Manipulator in an Uncalibrated Environment, IEEE, 2000, p. 635-645.

Lawson S.W. & Pretlove, Augmented Reality for Underground Pipe Inspection and Maintenance, Mechatronic Systems and Robotics Research Group, 1998, p. 1-7.

Roth H & Schilling K., Inspection and Repair Robots for Waste Water Pipes—A Challenge to Sensorics and Locomotion, IEEE, 1998, p. 476-478.

Schenker, Paul S., Advanced Man-Machine Interfaces and Control Architecture for Dexterous Teleoperations, IEEE, 1991, p. 1506-1525.

International Search Report for corresponding International Application PCT/US09/63129, Feb. 3, 2010.

Written Opinion for corresponding International Application PCT/US09/63129, Feb. 3, 2010.

Rokke, Petter, and Johan E. Hustad, "Exhaust Gas Recirculation in Gas Turbines for Reduction of CO2 Emissions; Combustion Testing with Focus on Stability and Emissions", Int. Journal of Thermodynamics, vol. 8, No. 4, pp. 167-173, Sep. 2005.

International Search Report for corresponding International Application PCT/US06/01983, Mar. 6, 2008.

Written Opinion for corresponding International Application PCT/US09/01983, Mar. 6, 2008.

Jinno et al., Force Controlled Grinding System for Unstructured Tasks, IEEE, 1992, p. 1117-1124.

Vukobratovic et al., Contact Control Concepts in Manipulation Robots-An Overview, IEEE, 1994, p. 12-24.

Zeng et al., An Adaptive Control Strategy for Robotic Cutting, IEEE, 1997, p. 22-27.

* cited by examiner

MANHOLE MODELER USING A PLURALITY OF SCANNERS TO MONITOR THE CONDUIT WALLS AND EXTERIOR

CROSS-REFERENCE TO RELATED APPLICATION

This application claims the benefit under 35 U.S.C. §119 (e) of the earlier filing date of U.S. Provisional Application Ser. No. 60/844,978 filed on Sep. 15, 2006.

BACKGROUND OF THE INVENTION

1. Field of the Invention

The present invention relates generally to apparatuses and methods for the inspection of access structures, vertical shafts, tunnels, and other conduits, and more specifically, to apparatuses and methods for the inspection of manholes to catalog their locations and general conditions including size, shape, appearance, structural condition (e.g., manhole ring, walls, and inverts), and location of lateral connections.

2. Description of the Background

Manholes provide access to sewer systems at the surface and extend down to sewer pipes. Manholes and other access structures are essential to the ongoing inspection, maintenance, and renovation of sewer systems. Inspection of manholes provides valuable information for maintenance and repair of sewer systems. Prior art methods of manhole inspection, however, do not provide comprehensive, repeatable, and measurable inspections.

Although practices for manhole inspection have not been standardized, practices and procedures for pipeline inspection have been well established. Oversight organizations in the United States such as the National Association of Sewer Service Companies (NASSCO) have developed defect codes to provide standards for the way in which defects in pipes are classified and rated. These standards are used to develop inventories of assets and conduct condition assessments of those assets using a standard approach. Standardization not only provides a better opportunity for data quality control, but also extends the shelf life of the data, leverages the use of data for many more purposes and creates an environment to actually monitor the rate of deterioration over time.

Inspection methods for pipes gather data in a manner to take advantage of those standards. These methods include the use of a remotely controlled, tethered mobility tractor or sled, a color, pan, tilt, zoom camera, and sometimes a light-based sensor to accurately measure pipe internal characteristics. A payout sensor mounted near a cable storage reel provides distance down a pipe in order to tag defects to a known location in the pipe. These methods are accepted in the industry to provide inspection data that can be analyzed to NASSCO standards.

While NASSCO has released a set of defect codes and rating standards that relate to manhole inspection, no current method provides thorough, consistent, and repeatable inspection of manholes. Current methods thus do not take advantage of those standards.

Traditional manhole inspections have been more of a survey, with inspectors looking for signs of water infiltration during wet weather events. The purpose of those surveys is to identify which manhole covers could be repaired or replaced to reduce infiltration problems.

Manhole inspections are performed to inventory collection system assets, to update collection system maps and to determine the structural condition of each manhole. Much of manhole inspection performed to date has been conducted by specialty firms that have individualized processes for collecting and interpreting manhole condition data. Those data are typically intended for specific project use and not for long term asset management. Differences in terminology, inspection forms, amount of detail, training, and database formatting generate condition assessment data that are inconsistent and difficult to use and compare. As with pipe inspection, manhole inspection can greatly benefit from a consistent approach to data collection and analysis.

Methods used to collect inspection data also vary widely. The least sophisticated and most dangerous of these methods is human entry into the manhole. This is less than desirable, as the inspector's safety is jeopardized by the confined space entry. Further, observations that are made are subjective in nature. In addition, no image data is typically recorded.

Some prior art approaches employ photography and camcorders along with flashlights and spotlights to collect visual inspection data from the ground level. This approach is safer for the inspector, but limits the ability to thoroughly inspect and identify all defects, some of which may be at the bottom of the manhole and difficult to assess from ground level. It is also very difficult to collect comprehensive image data so that the entire manhole is recorded in detail. In this scenario, the inspector still subjectively identifies and photographs defective areas of the manhole.

Another current practice for manhole inspection involves the use of a pan, tilt, zoom camera with lights mounted to the end of a telescoping pole. This device is lowered into manholes from ground level and provides better imagery. This method improves on previous approaches by collecting images at various elevations, theoretically allowing a more thorough inspection. However, this approach is still inadequate, as distance to the defect from ground level is not accurately determined. Distance is estimated or a tape measure is placed in the manhole and shown in the image to provide a reference.

All of the above methods fall short of providing a comprehensive, repeatable, and measurable inspection method. First, data from the entire manhole cannot be readily captured by photographs and/or video in sufficient detail. Comprehensive image assessment of the manhole interior allows for proper inspection verification and validation and time-based analysis. Second, traditional methods of manhole inspection fail to generate accurate, measurable data. Such information is valuable when deciding on suitable rehabilitation methods such as liners, inserts, or spray coatings. Further, the data that are captured are not easily stored or integrated into existing sewer asset management software or Geographic Information System (GIS) database systems.

Furthermore, each inspection typically results in a manhole inspection form being filled out by hand and provided to the customer. The customer form is completed by the contractor providing the inspection, with hand-drawn graphical representations of lateral connections, missing bricks, structural damage, and the like. Images are appended to the report as evidence of the defects located during inspection. Engineers can only interpret the results that the inspector has recorded. The engineers cannot validate or verify the inspection unless the inspection were repeated and witnessed at the time of inspection.

Thus, there has been a long-standing need for accurate, comprehensive, and repeatable inspection of manholes and other substantially vertical voids. By providing comprehensive imaging and integrated data collection, the present invention provides thorough manhole inspection data that can be standardized and used to monitor conditions over time. Further, the present systems, apparatuses, and inspection methods could be expanded to a wide variety of voids or conduits in addition to manholes.

SUMMARY OF THE INVENTION

The present invention provides systems, apparatuses, and methods for thorough, measurable, accurate, and repeatable collection of inspection data for manholes or other voids. A sensor head is suspended and lowered into a manhole or other void. The sensor head collects data related to the condition of the manhole or void walls, and locations of defects, damage, or lateral pipe openings. The data may be processed to provide a three-dimensional model of the manhole or void. Data regarding the location of the inspection may also be recorded to provide an abstract data set that can be used to compare previous or future data.

By providing such systems, apparatuses, and methods, the present invention further allows for standard defect coding according to NASSCO defined manhole defect codes and ratings. The present invention preferably employs high-resolution digital cameras, wide angle lenses, LED lighting, structured light, Differential Global Positioning System (DGPS), lasers, radar, sonar, and/or additional sensors to enable precision control during the inspection process.

Once the images and other data are gathered, an analysis of the data may be performed to assess the location and structural integrity of the manhole. The data that are gathered could be reviewed on-site for immediate analysis by qualified personnel or the data may be stored and/or transmitted off-site for analysis. In either method, the inspection equipment preferably may be readily moved to another manhole location to perform another inspection.

In its many disclosed preferred embodiments, the present invention provides manhole inspection systems, apparatuses, and methods for using those systems and apparatuses that use sensors suspended in manholes to collect data regarding the condition of manholes and surrounding structures. The sensors may collect data regarding the size and shape of a manhole, the location and nature of defects or damage, and the location and condition of lateral pipe connections. Such data may then be processed to create a model of the manhole that may be used to make maintenance or repair decisions. Further, such data can be used to compare changes in manhole conditions over time.

BRIEF DESCRIPTION OF THE DRAWINGS

For the present invention to be clearly understood and readily practiced, the present invention will be described in conjunction with the following figures, wherein like reference characters designate the same or similar elements, which figures are incorporated into and constitute a part of the specification, wherein.

DETAILED DESCRIPTION OF THE INVENTION

It is to be understood that the figures and descriptions of the present invention have been simplified to illustrate elements that are relevant for a clear understanding of the invention, while eliminating, for purposes of clarity, other elements that may be well known. The detailed description will be provided herein with reference to the attached drawings.

The present invention, in a variety of preferred embodiments, provides systems, apparatuses, and methods for the comprehensive inspection of manholes or other vertical or substantially vertical conduits. An apparatus that includes multiple sensors is lowered into a manhole or other conduit. The apparatus is adapted to collect data related to the status of the conduit, including the condition of the surface of the conduit walls, the condition of the walls themselves, the condition of the earth or materials surrounding the conduit walls, or the condition and location of other structures connected to the conduit. Such data may also include information regarding the locations of defects, damage, or lateral openings. As discussed in greater detail hereinbelow, the present invention may include particular ensembles of sensors depending on the type of data that is to be collected. Through data analysis and evaluation, an abstracted three-dimensional model of the manhole or conduit may be constructed.

Data regarding the location of the inspection may also be recorded, thus providing a real-world estimate of the location of the manhole or other conduit that is capable of being incorporated into third-party data management systems (e.g., GIS data sets) thus providing for a repeatable process that can be used to compare the progression of the state of the manhole or conduit over time.

The present invention is preferably described herein with reference to preferred embodiments that are used in the evaluation of manholes. Those descriptions are simply exemplary and should not be construed as limiting. One of skill in the art would equally recognize that the present invention could be applied to a wide variety of other substantially vertical conduits, such as boreholes, mine shafts, subway tunnels, ductwork, industrial piping, and other conduits.

Figure 1:
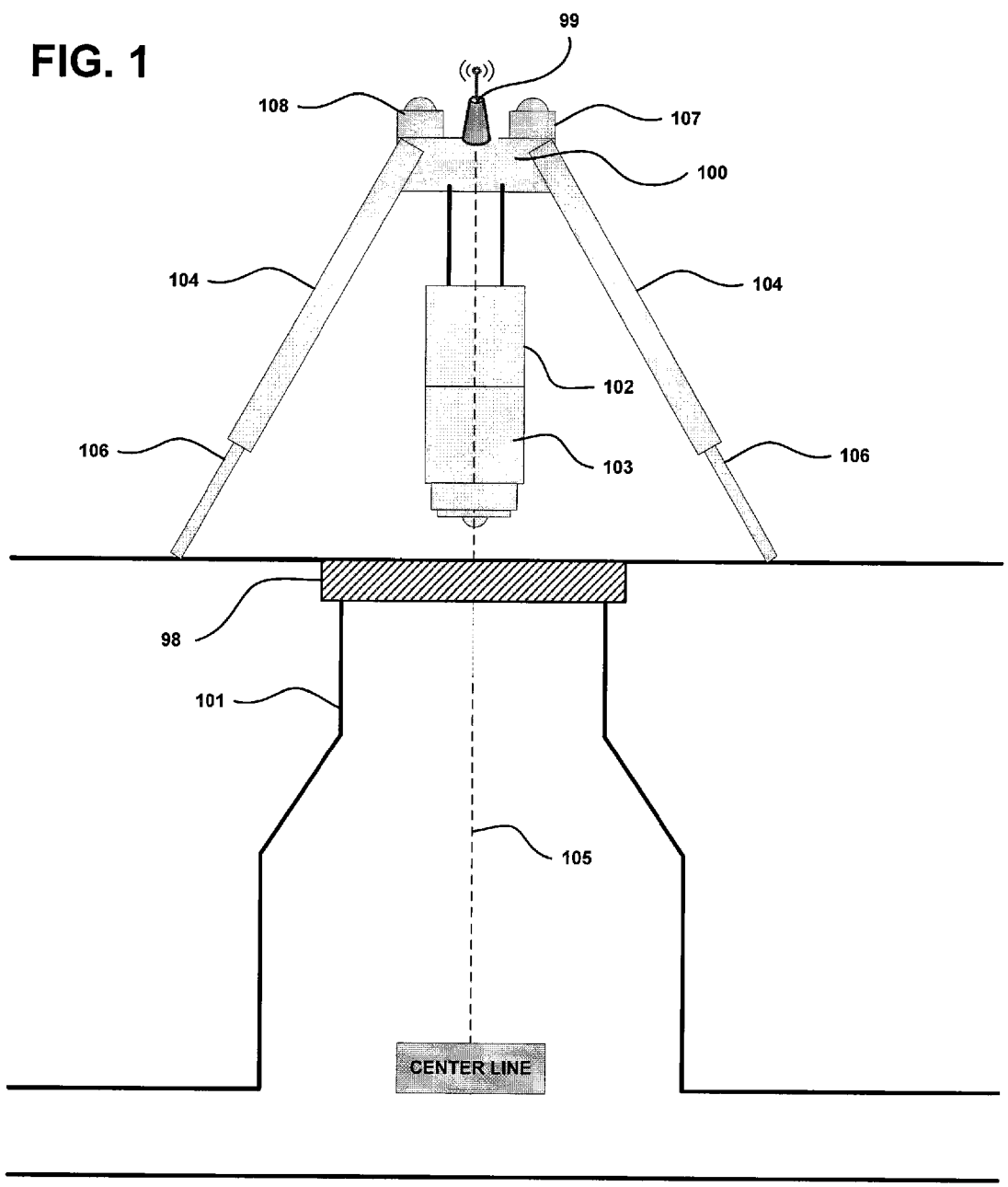
FIG. 1 shows an exemplary inspection apparatus and anchoring mechanism of the present invention.

In at least one preferred embodiment, shown in FIG. 1, the apparatus used to inspect conduits consists of a delivery mechanism 102 and a sensor head 103. An anchor mechanism preferably anchors the device over the manhole 101, thereby allowing the sensor head and delivery mechanism to be lowered into the manhole to be examined. A delivery mechanism 102 connects to an anchor mechanism at an anchor point 100, lowers the sensor head into the manhole, and suspends the sensor head in the manhole. The sensor head contains a plurality of sensors that collect data within the manhole.

The anchor mechanism is preferably relatively lightweight, portable, and rigid while at the same time not interfering with data collection. In one preferred embodiment, the anchor mechanism is a tripod 104 that resides above the manhole 101. The tripod 104 may be manually positioned by a user over the center of the manhole opening. To approximate the center of the manhole, a plumb line 105 may be used or the legs may be equally spaced around the manhole. Additionally, the tripod preferably has adjustable legs 106 to compensate for uneven ground conditions during operation. In another presently preferred embodiment, the tripod legs are designed to lock onto the rim 98 of the manhole, providing an accurate and repeatable registration of the manhole location.

A two-axis tilt sensor 107 or bubble level mounted at the anchor point 100 may be used to adjust the legs of the tripod until the anchor point 100 is level with respect to gravity. Alternatively, a two-axis gimbal mechanism may serve to normalize the anchor point 100 with respect to gravity and provide repeatable data collection.

A compass 108 may also be placed at the anchor point 100 to orient the anchor point 100. Gravity and the Earth's magnetic field provide a constant reference frame for a repeatable setup process, which allows for accurate correlation of inspection data to prior or future inspection data. An optional differential global position sensor 99 can also be placed at the anchor point 100 to provide the absolute position of the anchor point 100. Alternatively, a hand-held GPS device can be used to provide an accurate location.

In yet another preferred embodiment, the anchoring mechanism is an anchor bar spanning the manhole and attached below the manhole cover. The inspection apparatus may alternatively be anchored by any mechanism that allows the delivery mechanism to deliver the sensor head into the manhole.

As images above the manhole ring are typically part of a comprehensive inspection, the anchor mechanism preferably allows the sensor head to rise above the manhole opening. For a cable-based delivery mechanism, a small, raised structure, similar to a tripod, centered over the manhole and several feet tall may be used. If a rigid telescoping vertical boom is the preferred delivery mechanism, a larger tripod frame may be employed. Such anchor mechanisms may be mobile by means of wheels or a dolly. Alternatively, they may be mounted on the bumper of a truck.

The delivery mechanism is preferably intimately associated with the sensor head and is adapted to allow the sensor head to move vertically through the manhole ring down to the bottom of the sewer invert and back. The delivery mechanism preferably provides stiffness and stability to the sensor during motion. The delivery mechanism further collects data to determine the distance below the manhole ring to the sensor head, much in the same way that pipe inspection provides the distance into a pipe to a camera. The mechanism may be a motorized telescoping boom, cable-based system, or other appropriate mechanism for delivering the sensor head into a manhole.

In presently preferred embodiments, the delivery mechanism is a cable hoist using a spool or reel attached to the sensor head. Preferably, the spool or reel is motorized such that it may drive the sensor head up or down the manhole as desired. In other preferred embodiments, the delivery mechanism may be an articulated arm having multiple axial joints having numerous degrees of freedom. In another preferred embodiment, a motorized telescoping boom using a nested tube approach is used. One of skill in the art will recognize numerous other implementations of the delivery mechanisms depending on the specific circumstances under which the apparatus is to be employed.

In a presently preferred embodiment, a two cable hoist provides a lifting/lowering approach that is often employed by cranes. A gyroscopic mass may be added to increase stability of the system. Alternatively or additionally, the sensor head may be delivered via a cable or cables anchored to the bottom of the manhole for added stability. Such an embodiment may be employed for deep vertical inspections.

The delivery mechanism preferably provides vertical motion feedback in order to record distance down the manhole. This can be accomplished by encoders on drive motors which translate motor rotation into distance. Alternatively, ranging lasers can be used to calculate the distance from the surface. Additionally, an inertial measurement unit (IMU) may be used to measure and correct for any motion disturbances which could cause variability in the data.

Figure 2:
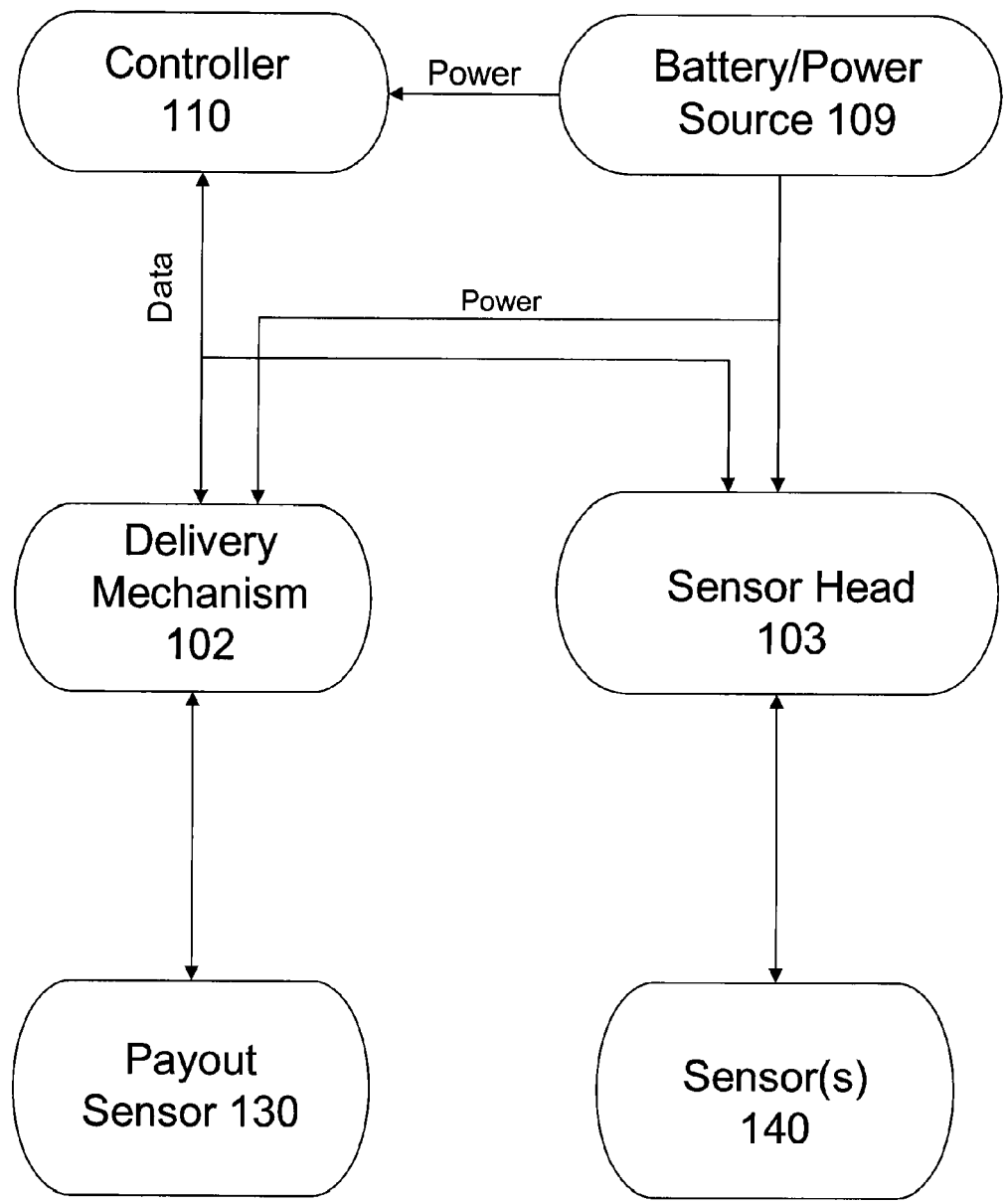
FIG. 2 is a schematic diagram of an exemplary inspection apparatus of the present invention.

FIG. 2 is a schematic diagram of an exemplary inspection apparatus of the present invention. A remote or on-board power source 109, such as a battery, provides power to a controller 110, delivery mechanism 102, and sensor head 103. The controller 110 may receive data from and transmit data to the delivery mechanism 102, sensor head 103, payout sensor 130, and/or other sensor(s) 140. The controller 110 may be located on-board with the sensor head 103. Alternatively, the controller 110 may remain above ground during an inspection and the data may be transmitted from the sensor head to the controller.

The sensor head preferably has several attributes. First, the sensor head may preferably take images of the manhole, providing comprehensive imaging of internal surfaces of the manhole. In one preferred embodiment, this is accomplished through a mega-pixel digital camera fitted with a fisheye lens. The fisheye lens preferably provides a viewing angle of at least 180-degrees, capturing a hemispherical image each time a picture is taken. Because there may be no optics for zooming-in as in typical pan, tilt, zoom cameras, the resolution is preferably great enough to allow for digital zooming without loss of image clarity. Consequently, lighting is preferably sufficient to illuminate the entire internal circumference of the manhole. This is preferably accomplished with a high-current LED light ring surrounding the fisheye lens.

A second camera, fisheye lens, and light assembly may optionally be added such that one camera assembly looks down the manhole and the second camera assembly looks up out of the manhole. Such embodiments capture a spherical image of the manhole with multiple points of view. While the downward-pointing camera assembly may effectively capture images down pipes that exit the manhole at a downward angle, the upward-pointing camera assembly may effectively capture images up pipes that enter the manhole at an angle from above.

Second, the sensor head preferably takes measurements of the internal surfaces and features (e.g., laterals, missing bricks, etc.) of the manhole. In one preferred embodiment, a laser diode and refractive lens assembly is used to project one or several laser rings on the internal surface of the manhole. With LED lighting turned off, the digital camera captures an image of the projected laser light circle. Those images can then be processed to extract dimensional data.

In other embodiments, sensors such as ranging laser or spinning laser systems use time of flight principles to gather dimensional data. In certain preferred embodiments, a ranging laser may be used to determine distance to the bottom of the manhole as a safety measure and to facilitate automation. In yet another embodiment, profiling sonar may be used to give an approximate shape and size of the manhole. Profiling sonar may be useful in conduits that may be partially or fully charged, i.e. filled with water or other fluid. Other sensors that may be used in conjunction with the present invention include, but are not limited to, point lasers, two-dimensional lasers, three-dimensional lasers, and radar.

Third, the present invention optionally includes sensors adapted to examine the internal conditions of conduit walls and conditions outside conduit walls. Such an examination may be accomplished using methods such as ground penetrating radar (GPR), surface penetrating radar (SPR), or ultrasonic testing. Specifically, such methods may be used to evaluate the integrity, composition, and thickness of manhole walls. Such methods may detect cracks or other defects and flaws within manhole walls or industrial piping. Further, such methods may be used to examine ground conditions surrounding manholes or other conduits. For example, such methods might detect or determine voids, soil composition, or points of water infiltration surrounding manholes.

Figure 3:
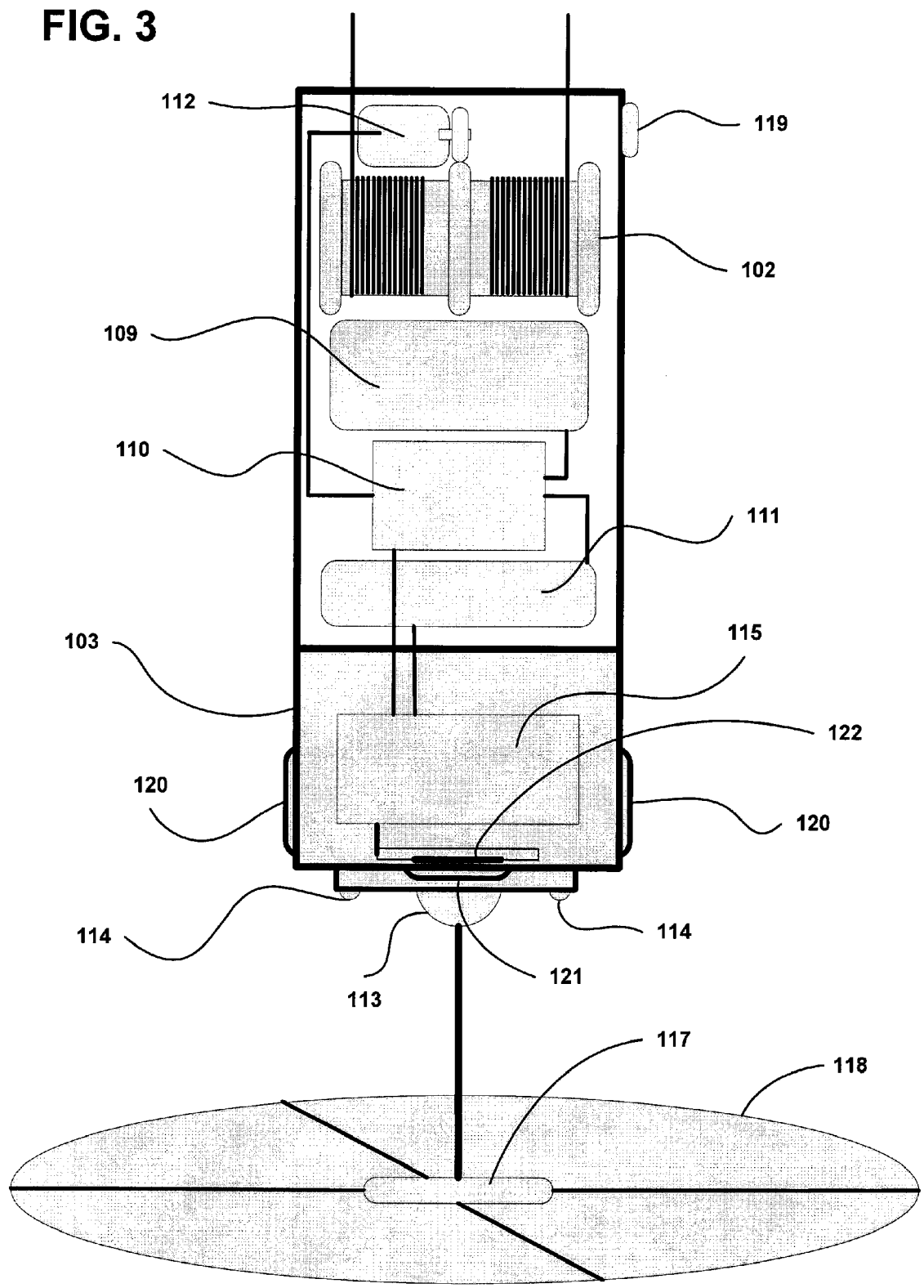
FIG. 3 shows an exemplary inspection apparatus of the present invention.

In one preferred embodiment, shown in FIG. 3, a cable hoist delivery mechanism 102 and sensor head 103 are powered by a removable and rechargeable battery 109. A microprocessor 110 runs embedded software to control the cable hoist's motor 112, calculates payout distance using motor-mounted encoder(s), and writes the data retrieved from the sensor head 103 and motor mounted encoder to an on-board removable storage media 111.

Attached to the cable hoist 102 is the sensor head 103. In one preferred embodiment, the sensor head includes a high-resolution fisheye lens camera that provides a 180-degree view of the manhole. The sensor head 103 includes a digital camera imaging board 122 capable of capturing high-resolution images and variable resolution real time video streams mated to a mega-pixel fisheye lens 113. The lens 113 is preferably surrounded by a ring of LED lights 114 that illuminate the manhole when taking an image or capturing video.

The sensor head 103 may also include a laser ring generator 117, preferably several inches in front of the fisheye lens 113. The laser generator 117 radially projects a ring of laser light 118 out to the manhole walls in a horizontal plane. The laser ring, being visible, is captured and recorded in digital images or video. By analyzing the laser rings 118 in each image or frame of video, the size and shape of cross-sectional slices of the manhole may be calculated.

A high-speed computational board 115 digitally captures images and compresses the size of high-resolution video streams so that they can be written to the removable media storage 111. Communications among the sensor head 103, cable hoist 102, microprocessor 110, and other components may be a hard-wired link, a wireless link, or other appropriate communications link. In certain preferred embodiments, the data are not stored on the sensor head, but are rather sent to a media storage device above ground using a wireless transmitter.

A radial proximity sensor 120 is preferably mounted on the sensor head in the same plane as the camera imaging board 122. The radial sensor 120 is used to determine when the camera has passed the plane of the manhole opening, providing a zero-reference point for payout distance.

The apparatuses of the present invention may be used to perform an automated manhole inspection. In such embodiments, the apparatuses of the present invention may take advantage of a plurality of sensors and data collection devices to evaluate conditions in and around a conduit. By assessing the data, the systems and apparatuses of the present invention preferably develop a three-dimensional assessment of the conduit autonomously.

The inspection may begin when the operator presses a power button 119 on the apparatus thereby activating the apparatus. The microprocessor 110 boots and loads software that starts the inspection. The software may be programmed to execute inspections according to a variety of parameters. For example, the microprocessor 110 may control the speed at which the sensor head is moved through a manhole, the number of times a given location is scanned, or the type and sequence of scanners that are used. The microprocessor 110 may also operate on a feedback loop to signal the sensor head 103 to continue scanning until image data of a certain quality is achieved.

In one preferred implementation, the microprocessor 110 commands the sensor head 103 to turn on the LED light ring 114 and the camera 122. While the computational board 115 captures high-resolution video, the microprocessor signals the delivery mechanism motor 112 to lower the sensor head 103 down the manhole. Live video may be continuously and digitally captured, compressed, and written to the storage media 111 as the sensor head is lowered. When the sensor head's radial proximity sensor 120 is triggered by the sensor passing through the manhole rim, the recorded payout distance may be set to zero, previous distances may be set to negative, and subsequent distances may be recorded as positive in the down direction.

In a currently preferred embodiment, a downward-looking ranging proximity sensor 121 is also mounted on the sensor head. The downward-looking sensor 121 senses the distance to the bottom of the manhole. The sensor head continues to descend while capturing video. The microprocessor 110 monitors the downward-looking proximity sensor 121 to determine when the bottom of the manhole has been reached. At a preset distance from the bottom of the manhole, the microprocessor 110 signals the delivery mechanism 102 to stop.

In one preferred embodiment, the microprocessor 110 may then activate various sensors to collect additional data regarding the manhole surfaces, walls, and surrounding environment. In particularly preferred embodiments, the microprocessor 110 may signal the sensor head to turn off the LED lights 114 and turn on the laser ring generator 117 so that a laser ring is being projected on the wall of the manhole 118.

The microprocessor may then signal the delivery mechanism to reverse directions and raise the sensor head 103 from the manhole. The camera 122 captures video of the laser ring 118 projected on the manhole walls. This video includes the laser ring image, which is digitally captured and stored in the same fashion as the previous video. The sensor head continues to travel upward until it passes the plane of the manhole and ends at the same elevation at which it started. At this point, the inspection is complete and sensor data has been written to the storage media 111. The storage media 111 and batteries 109 may remain in the delivery mechanism for several subsequent inspections, or they may be replaced with fresh batteries and an empty storage media device as power or space limitations dictate.

Data which is associated with the anchor mechanism, such as pitch and roll (2-axis tilt), compass heading, and DGPS may be manually recorded and combined with the data collected by the delivery mechanism and sensor head. Alternatively, before or after the manhole inspection begins, the anchor mechanism sensor suite may be physically connected to or may wirelessly transmit data to the delivery mechanism. Since the anchor mechanism data may be static, information need only be transmitted once or for a limited period of time. Preferably, such data would be transmitted at the beginning and end of the inspection to verify that the anchor point did not move during inspection.

Since the inspection system is preferably portable and preferably provides quick setup and data collection, the system is preferably self-contained to reduce the number of wires or power cords between the sensor head, the delivery mechanism, and the anchor mechanism. One of skill in the art will recognize multiple manners of implementing different strategies that are possible to accomplish those properties depending on the delivery mechanism implemented.

In one preferred embodiment utilizing a cable-based hoist system, a cable reel is located with the sensor head. A battery power source and removable solid state memory device such as compact flash are located on-board the sensor head to eliminate the need for power and data transmission lines. The payout distance of the cable reel is recorded directly to the on-board data storage device along with the associated images and other sensor data. The data are stored on-board the sensor head until the inspection is complete. The data may then be downloaded to a different storage medium through a physical port. Alternatively, the data may be wirelessly transmitted to a different storage medium or over a wireless phone or internet connection to a central location for processing.

If the delivery mechanism is a telescoping boom, power and data cables may run along the inside of the boom, providing the communication links needed. Alternatively, a wireless transceiver at the sensor head and at the anchor point can serve to transmit the data between the sensor head and delivery mechanism. The data may then be downloaded via physical port or transmitted wirelessly for post processing.

Communication between the delivery mechanism and sensor head facilitates the matching of sensor data with payout data, DGPS data, heading or compass information, and/or other data. When the delivery mechanism is located with the sensor head, as with a cable reel located with the sensor head, communication is easily established. If the delivery mechanism and sensor head are separate, as may be the case with a telescoping boom or cable reel located topside, then cabling or wireless transmissions may be used to provide communication between the delivery mechanism and sensor head.

In cases where cabling is not practical and wireless transmission will not suffice, an alternative method may be employed. In one preferred method, a "sensor processing" enclosure is fitted to the delivery mechanism. The sensor processing enclosure contains a battery and microprocessor with memory, acquires encoder ticks, calculates payout distance and records the data according to an accurate time stamp. Collected data may include tilt, heading or compass direction, or DGPS location. Simultaneously, the sensor head acquires sensor data and records the data with an accurate time stamp. The sensor enclosure's microprocessor's real time clock is preferably synchronized with the sensor head's real time clock. The delivery mechanism's payout distance can thus be mapped to sensor head data by matching time stamps of the two devices.

In another preferred embodiment, the manhole inspection apparatus is at least partially autonomous. A person may set up the anchor mechanism, attach the delivery mechanism and sensor head, and initiate the inspection. The inspection may then proceed with the data collected by the apparatus driving the inspection, as described herein. A PDA, laptop computer, or other dedicated device may be used to download the data from the sensor head when the inspection is complete.

Alternatively, tele-operated versions of the inspection are possible. In such operations, an operator monitors sensor and image data transmitted in real time from the sensor head to a monitor or other display. Data may be transmitted via a hardwired connection or wireless connection. The operator might determine and control how far to move the sensor head, how quickly to move the sensor head, which sensors to activate, when images are captured, light intensity, or a wide variety of other inspection characteristics.

Another preferred embodiment of the invention is adapted to inspect horizontal conduits in addition to manholes. In such an embodiment, an autonomous pipe inspection robot is tethered by a cable to an anchor point over or in a manhole. Some examples of such robots are disclosed in U.S. patent application Ser. No. 11/335,176 entitled "Autonomous Inspector Mobile Platform," which is hereby incorporated by reference. The robot is deployed down the manhole and into a pipe for inspection. Following inspection of the pipe, as described in U.S. patent application Ser. No. 11/335,176, the robot is retrieved from the pipe back into the manhole. The robot suspended by the cable tether then acts in the same manner as the sensor heads described herein and can be used to inspect the manhole. The robot may include the additional sensors and features of the sensor heads disclosed herein to provide the continued functionality of pipe and vertical conduit inspection.

After collecting data from the manhole, it may be stored on removable media storage in the delivery mechanism or sensor head. The storage media may be removed from the delivery mechanism or sensor head for direct download to a computer, removed for transfer to a data processing facility, or left in the delivery mechanism or sensor head for data download to another device that may provide a means to view the data, process the data, code defects and/or generate a report.

Data Processing

Data are preferably processed to generate an inspection report. Processing of image data may include corrections for brightness, contrast, or other parameters that may be digitally altered to improve the appearance of the image without destroying inherent data content. Next, the images may be de-warped, a process used to re-map the digital pixels to reverse the distortion caused by the images being passed through a fisheye lens. This correction improves the appearance of video or still images and corrects the shape of the laser ring that is captured through the lens.

Furthermore, the images may also be unrolled or flattened to improve the performance of software algorithms that can automatically detect defects and flaws. Additionally, end customers often prefer this unrolled view over a "down pipe" view.

Software may be programmed to detect defects by recognizing data anomalies. For example, software may be programmed to recognize certain digital pixel image characteristics as associated with water infiltration. Other software might analyze structured light laser scans and detect a data "hole" that might represent a missing brick. Alternatively or in addition to software defect detection, defects can be manually identified by reviewing inspection data.

Other acquired scanning data may be combined with video data. For example, payout sensor information may be combined with time, heading, and DGPS data to give locations of defects with respect to manhole and world coordinate systems referenced to a place and time.

Further, the images may be defect coded. This coding may be done manually or via software automation. The coding may be done by personnel qualified in the NASSCO Manhole Assessment and Certification Program. These data may then be embedded with image data to provide multi-dimensional indexing of the images with temporal (time), spatial (payout), contextual (manhole observations), and feature (defects) data.

These meta-data which is associated with the image may be added to a database such that it may be searched, sorted, and queried. For example, one could search for and display all images that have the defect of "missing brick" within 12 inches of the manhole entrance, and software may be adapted to find all the valid instances responsive to the query.

Such data are also useful for time-based analysis of manhole conditions. For example, time-based analysis may be used to verify the quality of spray liner coatings used to seal and rehabilitate manholes. Spatial data (e.g., payout data) may be used to match pre- and post-rehabilitation data from the same location. By comparing data from a pre-spray inspection with data from a post-spray inspection, the thickness, uniformity, and quality of the coating can be determined.

Time-based analysis can also be used to monitor structural changes in manhole conditions. For example, comparison of periodic inspection data from the same locations may reveal developing structural problems or trends in deterioration. Such information may be useful in making decisions regarding rehabilitation or preventive measures.

Spatial data may also be used to facilitate monitoring of specific defects in a given manhole. The spatial data may be used to target inspections to collect data only at the locations of selected defects. The spatial data may be used to quickly locate known defects for re-inspection. This may be accomplished, for example, by programming a controller with selected spatial data such that the sensor head collects data only at selected locations instead of executing an inspection of an entire manhole.

Laser images may be processed to determine the shape and size of the manhole. Knowing the distance between the camera's image plane and the laser and the number of pixels in an image, one may calculate the size of an object in that image. The process of counting pixels and measuring may be done by computer vision software that finds the laser circle in the image. Precise measurements of conduit size, lateral size, water levels, holes or missing bricks, and offset joints can be taken from a single frame of captured video.

As each frame of video is analyzed, a digital profile of the manhole can be constructed. This profile may provide information such as ovality, flow capacity, circumference, surface area, lateral locations, invert direction, etc. These parameters are important to contractors or owners of the manhole in considering rehabilitation methods such as spray coatings, liners, inverts, and manhole inserts which preferably match up to the existing manhole exactly.

Further, laser scans may be pieced together to provide a three-dimensional model of the manhole that is fully interactive, such that the user can navigate through the manhole in a virtual sense. Each laser scan is preferably tagged with payout information when the laser image is taken. By arranging each scan in succession according to the payout distance, a series of cross-sectional slices provides a frame to which a surface may be added using three-dimensional modeling techniques. As more images or laser scans are taken, the cross-sectional slices become denser and the accuracy of the model increases.

In another example of combining data, by again aligning the data by payout distance, the three-dimensional geometry created from the laser can be overlaid with images from the fisheye lens camera, where the image is actually placed on top of the three-dimensional surfaces of the model. The new "photo-realistic," spatially correct model may allow direct three-dimensional measurements to be taken from features in the image.

The result of the data processing and defect coding may be a hard copy and or digital copy of the report. The report may highlight defect areas so that rehabilitation decisions may be made by the customer. Manhole profile and three-dimensional models may be generated at customer request. Preferably, all data gathered are entered into a GIS system directly with all relevant data fields.

Additional methods of analyzing inspection data and combining different types of data are equally applicable to the present invention. Many of those additional methods are disclosed in U.S. patent application Ser. No. 11/627,334 entitled "Spatio-Temporal and Context-Based Indexing and Representation of Subterranean Networks and Means for Doing the Same," which is hereby incorporated by reference.

Nothing in the above description is meant to limit the present invention to any specific materials, geometry, or orientation of elements. Many part/orientation substitutions are contemplated within the scope of the present invention and will be apparent to those skilled in the art. The embodiments described herein were presented by way of example only and should not be used to limit the scope of the invention.

Although the invention has been described in terms of particular embodiments in an application, one of ordinary skill in the art, in light of the teachings herein, can generate additional embodiments and modifications without departing from the spirit of, or exceeding the scope of, the claimed invention. Accordingly, it is understood that the drawings and the descriptions herein are proffered only to facilitate comprehension of the invention and should not be construed to limit the scope thereof.

What is claimed is:

1. A method for inspecting a conduit, the method comprising the steps of:
    associating a sensor head with a delivery mechanism, wherein said sensor head comprises a plurality of scanners;
    positioning said sensor head within said conduit using said delivery mechanism, further wherein said delivery mechanism is adapted to allow said sensor head to be suspended in said conduit;
    lowering said sensor head into said conduit;
    scanning an environment within said conduit using said plurality of scanners, wherein said scanning includes collecting data regarding walls of said conduit, and
    retrieving said sensor head from said conduit;
    wherein said data regarding said conduit also includes information regarding materials surrounding an exterior surface of said conduit.

2. The method of claim 1, further comprising the step of collecting data regarding a position of said sensor head within said conduit.

3. The method of claim 2, wherein said data regarding said conduit and said data regarding a position of said sensor head include synchronized time stamps.

4. The method of claim 1, wherein said sensor head is functionally coupled to an anchoring mechanism, wherein said anchoring mechanism is adapted to engage said delivery mechanism to suspend said sensor head within said conduit.

5. The method of claim 1, wherein said conduit is a manhole.

6. The method of claim 1, further comprising storing said data to a data storage device.

7. The method of claim 6, wherein said sensor head includes said data storage device.

8. The method of claim 1, wherein one of said plurality of scanners is selected from the group consisting of a laser-based scanner, a sonar-based scanner, a radar-based scanner, or an image-based scanner.

9. The method of claim 8, wherein said image-based scanner is a digital camera.

10. The method of claim 1, further comprising the step of fusing said data into a three-dimensional representation of said conduit.

11. The method claim 1, wherein said lowering step includes assessing a depth that said sensor head has traversed into said conduit.

12. The method of claim 1, wherein said data regarding said conduit includes information about wall surfaces of said conduit.

13. The method of claim 12, wherein said data regarding wall surfaces of said conduit includes information about defects in said walls, damage of said walls, or lateral pipe openings.

14. The method of claim 12, wherein said data regarding said conduit also includes information about wall structures of said conduit.

15. The method of claim 12, wherein said data regarding said conduit also includes GPS coordinates of said conduit.

16. The method of claim 1, wherein said data about walls of said conduit is obtained during at least one of the following:
    while said plurality of scanners are being lowered into said conduit; and
    while said plurality of scanners are being retrieved from said conduit.

17. The method of claim 1, wherein said at least one sensor head detects a bottom of said conduit by determining a distance between said sensor head and a bottom interior surface of said conduit.

18. An apparatus for inspecting a conduit, comprising:

at least one scanner for obtaining data about walls of said conduit;

at least one downward looking sensor for obtaining data about a distance between said apparatus and a lower surface of said conduit;

and a delivery mechanism adapted to receive data from a controller and adjust a depth of said apparatus within said conduit, wherein said controller is adapted to employ said data about said distance to control said depth of said apparatus within said conduit;

said apparatus further comprising at least one scanner for obtaining data about an environment surrounding an exterior surface of said conduit.

19. The apparatus of claim 18, further comprising a radial proximity scanner.

20. The apparatus of claim 18, wherein said delivery mechanism comprises a motorized cable hoist system.

21. The apparatus of claim 18, wherein said controller is located remotely from said apparatus.

22. The apparatus of claim 18, wherein at least one of said at least one scanner for obtaining data about walls of said conduit includes a laser ring generator.

23. The apparatus of claim 18, wherein at least one of said at least one scanner for obtaining data about walls of said conduit includes a fisheye lens camera.

24. The apparatus of claim 18, wherein said apparatus is an autonomous mobile robot.

* * * * *